(12) United States Patent
Sies (10) Patent No.: US 8,568,805 B2
(45) Date of Patent: *Oct. 29, 2013

(54) COGNITIVE FUNCTION (75) Inventor: Helmut Sies, Meerbusch (DE)

(73) Assignee: Mars, Inc., McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/396,244

(22) Filed: Mar. 2, 2009

(65) Prior Publication Data

US 2009/0182037 A1   Jul. 16, 2009

Related U.S. Application Data

(62) Division of application No. 10/392,641, filed on Mar. 20, 2003, now Pat. No. 7,514,107.

(60) Provisional application No. 60/366,363, filed on Mar. 21, 2002.

(51) Int. Cl.
*A61K 36/00* (2006.01)
*A61K 31/35* (2006.01)

(52) U.S. Cl.
USPC .................... 424/776; 424/725; 514/456

(58) Field of Classification Search
None
See application file for complete search history.

(56) References Cited

U.S. PATENT DOCUMENTS

| | | | |
|---|---|---|---|
| 5,554,645 | A | 9/1996 | Romanczyk, Jr. et al. |
| 5,925,355 | A | 7/1999 | Chatterjee et al. |
| 6,207,702 | B1 | 3/2001 | Schmitz et al. |
| 6,297,273 | B1 | 10/2001 | Romanczyk, Jr. et al. |
| 6,391,310 | B1 * | 5/2002 | Empie et al. .................. 424/725 |
| 6,929,808 | B2 | 8/2005 | Castillo et al. |
| 7,011,856 | B2 * | 3/2006 | Kosuna .......................... 424/750 |
| 2002/0086067 | A1 | 7/2002 | Choi et al. |
| 2003/0017998 | A1 | 1/2003 | Snow et al. |
| 2003/0087937 | A1 * | 5/2003 | Lindberg ...................... 514/343 |
| 2003/0180406 | A1 * | 9/2003 | Sies ................................ 424/776 |
| 2004/0260076 | A1 * | 12/2004 | Castillo et al. ..................... 536/8 |
| 2008/0161386 | A1 * | 7/2008 | French et al. ................. 514/456 |
| 2011/0263696 | A1 * | 10/2011 | Graves et al. ................. 514/456 |

FOREIGN PATENT DOCUMENTS

| | | | |
|---|---|---|---|
| JP | 02031646 | * | 2/1990 |
| JP | 10-245342 | | 9/1998 |
| JP | 2001-048797 | | 2/2001 |
| WO | WO 00/30666 | | 6/2000 |
| WO | WO 00/57707 | | 10/2000 |
| WO | WO01/49307 | | 7/2001 |
| WO | WO 01/78529 | | 10/2001 |
| WO | WO 02/14251 | | 2/2002 |
| WO | WO02/42429 | | 5/2002 |
| WO | WO02/076381 | | 10/2002 |
| WO | WO03/013442 | | 2/2003 |

OTHER PUBLICATIONS

Liu et al. J. Anti-Aging Med. 1999. vol. 2, No. 4, pp. 349-355.*
Youdim et al. Free Radical Biol. Med. 2001. vol. 30, No. 6, pp. 583-594.*
Hammerstone et al. J. Agric. Food Chem. 1999. vol. 47, pp. 490-496.*
Website Publication entitled "All About Pycnogenol". 4 pages. Downloaded from website http://www.quantumhealth.com/new/pycnogenol_about.html on Mar. 25, 2010.*
Soliman, K. F. A., et al., In vitro attenuation of nitric oxide production in C6 astrocyte cell culture by various dietary compounds, Proceedings of the Society for Experimental Biology and Medicine, 1998, vol. 218, No. 4, pp. 390-397.
Kazuo Shinya et al., Effects of Green Tea Catechin on Alzheimer's Disease; Tea, 50 (May), p. 6-10 (1997).
Shinya, Kazuo.
Peter C. H. Hollman, et al., "The Biological Relevance of Direct Antioxidant Effects of Polyphenols for Cardiovascular Health in Humans is Not Established", The Journal of Nutrition, Supplement: Antioxidant Activity of Polyphenols and Cardiovascular Risk—Application of the PASSCLAIM Criteria, 2011, American Society for Nutrition, pp. 989S-1009S, First published online Mar. 30, 2011.
Giovambattista Desideri, et al., "Benefits in Cognitive Function, Blood Pressure, and Insulin Resistance Through Cocoa Flavanol Consumption in Elderly Subjects With Mild Cognitive Impairment: The Cocoa, Cognition, and Aging (CoCoA) Study", Hypertension, 2012, vol. 60, pp. 794-801. Originally published online Aug. 14, 2012.

* cited by examiner

*Primary Examiner* — Chris R Tate
(74) *Attorney, Agent, or Firm* — Nath, Goldberg & Meyer; Sheldon M. McGee; Lakshmi Rajan (57) ABSTRACT

This invention relates to compositions containing polyphenols, for example, cocoa polyphenols such as flavanols and their related oligomers, and methods for treating abnormalities in gap junctional communication of cells, such as cancer, heart arrhythmia, neuro-degenerative diseases and cognitive dysfunction.

51 Claims, 5 Drawing Sheets

COGNITIVE FUNCTION

This application is a divisional application of the U.S. application Ser. No. 10/392,641, filed Mar. 20, 2003, which claims the benefit, under 35 U.S.C. Section 119, of the U.S. Provisional Application Ser. No. 60/366,363, filed Mar. 21, 2002, both of which are hereby incorporated herein by reference in their entirety.

FIELD OF THE INVENTION

This invention relates to compositions, and methods of use thereof, containing polyphenols such as procyanidins, for example, cocoa polyphenols such as cocoa procyanidins for treating, preventing, reducing the risk of, or reducing the occurrences of heart arrhythmias. The invention also relates to the compositions, and the methods of use thereof, containing polyphenols such as procyanidins, for example, cocoa polyphenols such as cocoa procyanidins for treating, preventing, reducing the risk of, or reducing the progression of neuro-degenerative, and other diseases involving defective gap junctional communication between cells, for example cognitive dysfunction.

BACKGROUND OF THE INVENTION

Cocoa polyphenols, such as flavanols and their related oligomers, have been shown to have beneficial effects on hypertension, atherosclerosis and cardiovascular disease. These effects are shown, for example, in the International Appl. No. PCT/US97/05693, published as WO97/36497, and the examples reported in the application. It has been shown therein that cocoa polyphenols can be used to treat or prevent conditions which are known to be affected by the administration of non-steroidal anti-inflammatory drugs, for example, aspirin. However, the use of cocoa polyphenols rather than aspirin for therapy and prophylaxis is advantageous because cocoa polyphenols do not have the side effects of aspirin, such as stomach bleeding.

A new use of cocoa polyphenols, such as flavanols and their related oligomers, has now been surprisingly discovered. The compositions and products disclosed herein may be used for the treatment, prophylaxis, reduction of risk of, and reduction of occurrences of heart arrhythmia. Moreover, these compositions and products may be used for treating, preventing, reducing the risk of, or slowing the progression of any condition associated with abnormalities in the gap junctional communication between cells such as cancer, heart arrhythmia, and neuro-degenerative and other diseases involving defective gap-junctional communication between cells.

SUMMARY OF THE INVENTION

The invention relates to compositions, products and methods for treating, preventing, reducing the occurrences of, or reducing the risk of heart arrhythmia in a mammal suffering from, or at risk of suffering from, heart arrhythmia, a human or a veterinary animal such as a horse, a cat or a dog. Moreover, the invention relates to methods and products for treating, preventing, reducing the risk of, or slowing the progression of any condition associated with abnormalities in the gap junctional communication between cells such as cancer, heart arrhythmia, neuro-degenerative diseases and cognitive dysfunction involving defective gap-junctional communication between cells.

In one aspect, the invention relates to a composition, such as a food, a food additive, a dietary supplement, or a pharmaceutical comprising a cocoa polyphenol. The composition may optionally contain L-arginine and/or a cholesterol reducing agent.

Packaged products containing the above-mentioned compositions and a label and/or instructions for use to treat, prevent, reduce the risk of, or slow the progression of heart arrhythmia, a neuro-degenerative disease or any condition associated with abnormalities in the gap junctional communication of cells are also within the scope of the invention.

In another aspect, the invention relates to a method for treating, preventing, reducing the risk of, or reducing the occurrences of heart arrhythmia in a mammal, such as a human or a veterinary animal, by administering a composition containing a cocoa polyphenol such as cocoa flavanols and/or its related oligomers to the mammal in need thereof.

In yet another aspect, the invention relates to a method of treating, preventing, reducing the progression of, or reducing the risk of a condition associated with the abnormalities in the cellular gap junction communication in a mammal, such as a human or a veterinary animal, by administering a composition containing a cocoa polyphenol such as cocoa flavanols and/or its related oligomers to the mammal in need thereof. For example, such condition is a neuro-degenerative disease or cognitive dysfunction and the mammal suffers or is at risk of suffering of the neuro-degenerative disease or cognitive dysfunction.

DETAILED DESCRIPTION

All patents, patent applications and references cited in this application are hereby incorporated herein by reference. In case of any inconsistency, the present disclosure governs.

The present invention relates to a composition containing a flavanol and/or its related oligomers, such as at least one cocoa flavanol and/or its related procyanidin oligomer, to a mammal in need thereof. The composition may optionally contain a cholesterol lowering agent, for example, a sterol and/or stanol based cholesterol lowering agent, L-arginine, calcium, potassium, magnesium, an antioxidant, for example vitamin E and vitamin C, any of the vitamins of the B complex, a carotenoid, guar gum, or a mono or polyunsaturated fatty acid (e.g. omega-3 fatty acid), vitamin D3, retinal, retinoids, soy protein and selenium. Compositions may contain polyphenols from sources other than cocoa, e.g. peanut skins, which have properties similar to those of cocoa polyphenols in addition to, or in place of, the cocoa polyphenols.

As used herein, the term "cocoa polyphenol" (CP) refers to a polyphenolic substance such as flavanols and their related oligomers present in cocoa beans or extracted from cocoa beans or cocoa ingredients. The term "flavanol" includes the monomers catechin and epicatechin. Oligomers of catechin and epicatechin are referred to as procyanidins. Any reference to cocoa polyphenol herein should be understood to also apply to cocoa flavanols and procyanidin, in combination and individually.

The term "cocoa ingredient" refers to a cocoa solids-containing material derived from shell-free cocoa nibs such as chocolate liquor and partially or fully-defatted cocoa solids (e.g. cake or powder).

The phrase "cholesterol lowering agent" means any compound, combination of compounds, an extract or a plant component, naturally found or processed, that has the property of lowering cholesterol levels in a mammal when administered in an effective amount. When such cholesterol lowering agent is a compound or a combination of compounds that is of a sterol or stanol type, i.e., including derivatives and isomeric forms, the cholesterol lowering agent is referred to as a "sterol and/or stanol based cholesterol lowering agent." When the phrase is used in reference to a composition, for example, "a cholesterol reducing dark chocolate," it means that the composition has the property of lowering cholesterol.

The cocoa polyphenols may be of natural origin, i.e., derived from a cocoa bean, or prepared synthetically. A person of skill in the art may select natural or synthetic cocoa polyphenol based on availability or cost. Cocoa polyphenols may be included in the composition in the form of a cocoa ingredient containing cocoa polyphenols, for example, chocolate liquor included in chocolate, or may be added independently of cocoa ingredients, for example, as an extract, extract fraction, isolated and purified individual compound, pooled extract fractions or a synthetically prepared compound.

The cocoa polyphenols include cocoa flavanols and their oligomers. Flavanols include (+)-catechin, (−)-epicatechin and their respective epimers (e.g. (−)-catechin and (+)-epicatechin) and have the structure:

The procyanidin oligomers may have from 2 to about 18, preferably from 2 to about 12, and most preferably from 2 to about 10 monomeric units. For example, oligomers may be dimers, trimers, tetramers, pentamers, hexamers, heptamers, octamers, nonamers and decamers. In the oligomer, monomers are connected via interflavan linkages of (4→6) and/or (4→8). Oligomers with exclusively (4→8) linkages are linear; while the presence of at least one (4→6) bond results in a branched oligomer. In the case of peanut skins polyphenols, linkages, such as C2→O→C7, are also present.

Thus, a polymeric compound of the formula $A_n$, or a pharmaceutically acceptable salt thereof, may be used in the compositions and methods of the present invention:

wherein n is an integer from 2 to 18, such that there is at least one terminal monomeric unit A, and one or a plurality of additional monomeric units;

R is 3-(α)-OH, 3-(β)-OH;

bonding between adjacent monomers takes place at positions selected from the group consisting of 4, 6 and 8;

a bond of an additional monomeric unit in position 4 has alpha or beta stereochemistry;

X, Y and Z are selected from the group consisting of monomeric unit A or hydrogen, with the provisos that as to the at least one terminal monomeric unit, bonding of the additional monomeric unit thereto is at position 4 and optionally Y=Z=hydrogen.

The cocoa polyphenol may be prepared by extraction from cocoa beans, cocoa nibs, or cocoa ingredients such as chocolate liquor, partially defatted cocoa solids, and/or fully defatted cocoa solids. Preferably, the extract is prepared from a fully or partially defatted cocoa powder. Beans from any species of *Theobroma, Herrania* or inter- and intra-species crosses thereof may be used. The extract may be prepared from fermented, underfermented or unfermented beans, the fermented beans having the least amount of cocoa polyphenols and the unfermented the most. The selection of beans may be made based on the fermentation factor of the beans, for example, the extract may be made from the beans having a fermentation factor of about 275 or less. Optimizing the level of polyphenols in the cocoa ingredient and extract thereof by manipulating the degree of fermentation may be done as described in the International Appl. No. PCT/US97/15893 published as WO98/09533, the relevant portions of which are hereby incorporated herein by reference.

Cocoa polyphenols may be extracted from cocoa ingredients that have been processed using traditional methods of cocoa processing (described, for example, in Industrial Chocolate Manufacture and Use, ed. Beckett, S. T., Blackie Acad. & Professional, New York, 1997, such as in Chapters 1, 5 and 6) or using an improved processing method described in U.S. Pat. No. 6,015,913 to Kealey et al. that preserves polyphenols (by preventing their destruction) in cocoa ingredients in contrast to the traditional methods. The improved cocoa processing method omits the traditional roasting step. Thus, cocoa ingredients obtainable by (a) heating the cocoa bean for a time and a temperature sufficient to loosen the cocoa shell without roasting the cocoa nib; (b) winnowing the cocoa nib from the cocoa shell; (c) screw pressing the cocoa nib and (d) recovering the cocoa butter and partially defatted cocoa solids which contain preserved levels of cocoa polyphenols, may be used. The method retains a much higher level of higher procyanidin oligomers than traditional processing methods. Cocoa solids produced by this method may contain greater than 20,000 μg of total flavanol and/or procyanidins per gram nonfat solids; preferably greater than 25,000 μg/g, more preferably greater than 28,000 μg/g, and most preferably greater than 30,000 μg/g. For purposes of this invention, the total flavanol and/or procyanidin amounts are determined as described in Example 2.

Cocoa polyphenols may be extracted from the sources indicated above using solvents in which the polyphenols dissolve. Suitable solvents include water or organic solvent such as methanol, ethanol, acetone, isopropyl alcohol and ethyl acetate. Solvent mixtures may also be used. When water is used as the solvent, it may be slightly acidified, for example with acetic acid. Examples of some solvents are mixtures of water and organic solvent, for example aqueous methanol, ethanol or acetone. Aqueous organic solvents may contain, for example, from about 50% to about 95% of organic solvent. Thus, about 50%, about 60%, about 70%, about 80% and about 90% organic solvent in water may be used. The solvent may also contain a small amount of acid such as acetic acid, for example, in the amount of about 0.5% to about 1.0%. The composition of the extracts, i.e., the representation (i.e., oligomeric profile) and the amount of procyanidin oligomers, will depend on the choice of solvents. For example, the water extract contains primarily monomers, the ethyl acetate extract contains monomers and lower oligomers, mainly dimers and trimers, and the aqueous methanol, ethanol or acetone extract contains monomers and a range of higher oligomers. One of the solvents for extraction of monomer as well as higher procyanidin oligomers is about 70% acetone. However, any extract containing polyphenols is useful in the invention. The methods of cocoa polyphenol extraction are known in the art and are described, for example, in the U.S. Pat. No. 5,554,645 to Romanczyk et al. and the International Appl. No. PCT/US97/05693, published as WO97/36497. Thus, in one embodiment, the cocoa extract is prepared by reducing cocoa beans to cocoa powder, defatting the powder, extracting the cocoa polyphenols, and purifying the extract. The cocoa powder can be prepared by freeze-drying the cocoa beans and pulp, depulping and dehulling the freeze-dried cocoa beans, and grinding the dehulled beans.

The cocoa polyphenol extract may be purified, for example, by removal of the caffeine and/or theobromine, and further purified by gel permeation chromatography and/or High Pressure Liquid Chromatography (HPLC). Gel permeation chromatography (e.g. on Sephadex LH-20) may be used to enrich the extract for higher procyanidin oligomers. For example, the eluate containing monomers and lower oligomers may not be collected until the oligomer(s) of choice begins eluting from the column. An example of such an extract is known in the art and is described in Example 5 of the International Appl. No. PCT/US97/05693, published as WO97/36497, the relevant portions of which are hereby incorporated by reference herein. By using preparative HPLC, for example, normal phase HPLC, the extract may be fractionated, for example, into monomeric and oligomeric fractions containing at least 50% by weight of the monomer or specific oligomer(s). When a particular fraction contains the monomers or any of the lower oligomers (e.g. dimers, trimers or tetramers fraction), the fraction contain about 90 to 95% by weight of the particular oligomeric fraction. The desired fractions may be pooled after separation to obtain a combination of oligomers of choice for example to contain oligomers 3-10 or 5-10. A person of skill in the art can manipulate the chromatographic conditions to achieve the desired procyanidin profile in view of the guidance in this specification, general knowledge in the art and, for example, the teachings of U.S. Pat. No. 5,554,645 to Romanczyk et al. and the International Appl. No. PCT/US97/05693, published as WO97/36497.

The monomeric fraction typically contains a mixture of monomers epicatechin and catechin; and the oligomeric fraction typically contains a mixture of dimers (in a dimer fraction), trimers (in a trimer fraction), tetramers (in a tetramer fraction), etc. Mixtures of monomers and oligomers occur in isolated fractions because cocoa contains more than one type of each of monomer, dimer, etc. The oligomeric variability occurs as a result of two monomers, epicatechin and catechin, that are building blocks of procyanidins, as well as the chemical bond connecting monomers in the oligomer. Thus, cocoa dimers are primarily B2 and B5, each of which contains two monomers of epicatechin. Individual monomers and oligomers may be obtained using reversed-phase HPLC, e.g. using a C18 column.

Cocoa polyphenol may be used in the compositions of the invention as a cocoa extract, e.g. solvent-derived extract, cocoa fraction, isolated compounds or in the form of a cocoa ingredient or a chocolate containing an effective amount of cocoa flavanols and/or procyanidins. The cocoa ingredients may be prepared using traditional cocoa processing procedures but is preferably prepared using the method described in U.S. Pat. No. 6,015,913 to Kealey et al. Alternatively, to enhance the level of cocoa polyphenols, chocolate liquor and cocoa solids prepared from cocoa beans having a fermentation factor of about 275 or less may be used. These ingredients have cocoa polyphenol content that is higher than can be obtained using traditional cocoa processing methods (e.g. with roasting) and fully fermented beans. The chocolate may be prepared using conventional techniques from the ingredients described above or using an improved process for preserving cocoa polyphenols during chocolate manufacturing as described in the International Appl. No. PCT/US99/05414 published as WO99/45788, the relevant portions of which are hereby incorporated herein by reference. A chocolate prepared by at least one of the following non-traditional processes is referred to herein as a "chocolate having a conserved amount of cocoa polyphenols": (i) preparing cocoa ingredients from underfermented or unfermented cocoa beans; (ii) preserving cocoa polyphenol during cocoa ingredient manufacturing process; and (iii) preserving cocoa polyphenol during chocolate manufacturing process.

In some embodiments, the compositions contain at least one oligomer, such as for example a dimer. Such compositions may additionally contain at least one monomer or a combination of monomers, e.g. catechin and epicatechin. In another embodiment, compositions containing a combination of monomers, catechin and epicatechin, e.g. in a form of a monomer fraction isolated from cocoa, are also prepared and used.

Synthetic procyanidins may also be used and are prepared by methods known in the art and as described for example in the International Appl. No. PCT/US98/21392 published as WO99/19319, the relevant portions of which are hereby incorporated herein by reference. Cocoa polyphenol derivatives may also be useful. These include gallated monomers and oligomers, glycosylated monomers and oligomers, and mixtures thereof, metabolites of the procyanidin monomers and oligomers, such as the sulphated, glucoronidated, and methylated forms; and enzyme cleavage products of procyanidins generated by colonic microflora metabolism or internal mammalian metabolism. The derivatives may be from natural sources or prepared synthetically.

The composition may optionally comprise a cholesterol lowering agent. Any cholesterol lowering agent irrespective of its mode of action may be used. Suitable agents may act by reducing cholesterol absorption in the bile of a mammal or by reducing cholesterol synthesis. Examples of suitable agents are phytosterols, phytostanols and their derivatives and isomers; soy protein; soluble fibers, e.g. beta-glucan from, for example, oat and psyllium, nuts, rice bran oil, each of which is particularly suitable for use in food, dietary supplements and food additive compositions. Known cholesterol reducing drugs may also be used but are less preferred for use in the food and food additive compositions, but may be used in a pharmaceutical. It will be obvious to a person of skill in the art that the choice of the cholesterol lowering agent depends on the intended delivery vehicle (e.g. food, supplement, pharmaceutical) and the mode of administration. Thus, an agent that reduces absorption of cholesterol in the bile will not be preferred for intravenous administration. Similarly, if the delivery vehicle is food, a cholesterol lowering agent having a strong medicinal taste or smell may not be desirable.

Phytosterols are plant sterols that do not dissolve in water and have the molecular weight and the structure similar to cholesterol. Phytosterol reduce cholesterol absorption in the bile (of both endogenic and dietary cholesterol) as well as serum cholesterol levels (total and LDL) without being absorbed themselves. Over forty plant sterols have been identified but beta-sitosterol, campesterol and stigmasterol are most abundant. Other examples of useful sterols are brassicasterol, desmosterol, chalinosterol, poriferasterol, an clionasterol. Individual sterols or a mixture of sterols, isolated from natural sources or synthetic, and isomers and derivatives thereof may be used. Particularly useful are saturated derivatives of sterols, known as stanols, in which all carbon-carbon bonds in the rings are saturated. Suitable stanols have 28 or 29 carbon atoms and include beta-sitostanol, clionastanol, 22,23-dyhydrobrassicastanol and campestenol. Phytosterols may be solid (e.g. powder, granules) or liquid (e.g. oil) form.

The sterols and stanols are found in several plant materials as described for example in the International Appl. No. PCT/EP96/02344. Exemplary sources of sterols/stanols are pine bark, soy oil, tall oil, bamboo shoot extract (described in the International Appl. No. PCT/US98/12556, published as WO98/57545), cocoa hulls and oil, and rice bran oil. Tall oil, a byproduct of the pulp and paper industry, is a good source of stanol, i.e., beta-stanol.

Plant sterol may be obtained from natural sources such as vegetative oils, vegetative oil sludge, vegetative oil distillates, and other plant oil sources such as tall oil by relatively simple and inexpensive means. For example, a preparation of sterols from vegetable oil sludge by using solvents such as methanol is described in U.S. Pat. No. 4,420,427 to Hamunen. Stanols are found in small amounts in nature but may be easily prepared from sterols by hydrogenating sterols by any of the several methods known to those of skill in the art. When a sterol starting material is prepared from a plant material it will contain a mixture of several different sterols thus, after hydrogenation, the resulting stanol will also be a mixture of different stanols. The mixtures are suitable for use in the present invention. However, pure specific sterol preparations may be hydrogenated as well to produce pure stanols that can also be utilized.

Cocoa oil extracted from cocoa hulls is a good source of phytosterol. Cocoa phytosterols are a mixture of free and bound sterols, with the free sterols being up to about 90% of the phytosterols present. The phytosterols include campesterol, β-sitosterol, stigmasterol, cycloartenoyl, 24-methylene cycloartenoyl, as well as minor amounts of other phytosterols. The bound phytosterols include the fatty acid esters or ferulate derivatives of the phytosterols. The cocoa oil also contains tocols, which include tocopherols (which have antioxidant properties) and tocotrienols (which may have cholesterol lowering activity. The cocoa oil is prepared by the process comprising the steps of: (i) grinding the cocoa hulls; (ii) extracting the ground cocoa hulls with a solvent for the phytosterols; (iii) removing the solvent; and (iv) recovering the cocoa oil. The cocoa hulls, a byproduct of the cocoa bean roasting, can be from dried fermented cocoa beans, micronized cocoa beans, roasted cocoa beans, and preferably from dried unfermented beans, which contain the highest total sterol content. The preferred cocoa beans are from *Theobroma cacao*. The preferred solvents are petroleum ether, hexane, pentane, and ethyl ether. The solvent may be recovered by vacuum distillation. In one embodiment, freeze dried hulls are ground to a fine powder with a Tekmar Mill (Cincinatti, Ohio) and the ground mass is subjected to an overnight extraction with redistilled petroleum ether (b. p. 38-39.6° C.) in a Soxtec apparatus (Fisher Scientific, Springfield, N.J.). The following morning, the solvent is carefully removed by slow evaporation under a stream of nitrogen, and the resultant extract is stored at −40° C. The phytosterols may then be purified by preparative HPLC or column chromatography.

Esterified forms of both sterols and stanols may also be used. Esterification renders the sterols/stanols more soluble in fats and oils, which may, in some instances, help their incorporation into food products or other delivery vehicles. For example, sterols may be esterified with fatty acid esters. Examples of such esterified sterols include sitosterol acetate, sitosterol oleate and stigmasterol oleate. Stanol esters may be prepared as is known in the art and for example as described in U.S. Pat. No. 6,031,118 to van Amerongen et al, U.S. Pat. No. 5,892,068 to Higgins, U.S. Pat. No. 5,502,045 to Miettenen et al, and the International Appl. No. PCT/CA99/00655 (published as WO00/04887). In one embodiment, useful stanol esters are prepared by esterifying at least one sterol with a $C_2$ to $C_{22}$ fatty acid ester as described in U.S. Pat. No. 5,958,913 to Miettenen et al. Other methods known in the art may be used to increase the solubility of sterols/stanols upon administration to a mammal. One such method is described in U.S. Pat. No. 5,932,562 to Ostlund, wherein the sterol/stanol is mixed with lecithin to obtain a water soluble powder.

Sterols/stanols may be added to the composition in powder form by mixing with other ingredients. In case of a food composition, stanol/sterols as well as other cholesterol lowering agents are conveniently added at the step of mixing. During the preparation of cholesterol lowering chocolate, for example, sterols/stanols may be added to the dry mix containing sugar, the melting butter; the nibs before milling; or the melted chocolate, which may be less preferred. To facilitate mixing, sterols/stanols may be first dissolved in a solubilizing agent such as fat, vegetable oil, monoglycerides, diglycerides, triglycerides, tocopherols and mixtures thereof. Effective carriers for making suspensions and emulsions of sterols/stanols are water, alcohol, polyol, other edible compounds, for example chocolate liquor, in which sterols/stanols are at least partially soluble and mixtures thereof.

Soy protein may be added to the composition in any known form, for example, it may be soy protein isolate, soy protein concentrate, textured soy protein or soy flour, flakes and grits. Whole grain or fragment thereof may also be used as described, for example, in Example 5. Various forms of soy protein are well known in the art and are commercially available. Its properties and methods of obtaining are described, for example, in Soy Protein and Human Nutrition, Wilcke et al., eds., Acad. Press, NY, 1979. Soy protein may be used in combination with any sterol and/or stanol based cholesterol lowering agent.

Soluble plant fibers, e.g. beta-glucan, are capable of reducing plasma cholesterol. The fibers for use in the present invention may be obtained from any source of beta-glucan, preferably oat grain and oat bran. The fibers may be prepared and added to compositions according to methods known in the art. They are particularly suitable for orally delivered compositions such as foods and dietary supplements. Beta-glucan and other soluble plant fibers may be used in combination with any sterol and/or stanol based cholesterol lowering agent.

The composition of the invention may also contain L-arginine, which may be provided in the composition of the invention in various forms, for example as a purified compound, an extract from an L-arginine containing plant, or in the form of a seed/nut ingredient, e.g. nut flour, or as an entire seed/nut. Any L-arginine source may be used, synthetic or natural. Preferred L-arginine sources are soy beans and nut meats such as peanuts, walnuts, almonds, and hazelnuts. Defatted and partially defatted nut meats may be used. These may be ground and are referred to as nut flour.

The composition may also contain calcium, potassium, magnesium, antioxidant such as vitamin E and vitamin C, any of the vitamins of the B complex, a carotenoid, guar gum, or a mono or polyunsaturated fatty acid (e.g. omega-3 fatty acid), which can be obtained according to the methods known in the art. The mono or polyunsaturated fatty acids may be used in the form of an olive oil, fish oil or a nut. Examples of nuts suitable for this use are: peanuts, almonds and walnuts.

The composition of the invention is useful as a food, a food additive, a dietary supplement, or a pharmaceutical. The compositions may contain a carrier, a diluent, or an excipient. Depending on the intended use, the carrier, diluent, or excipient may be chosen to be suitable for human or veterinary use, food, additive, supplement or pharmaceutical use.

As used herein a "food" is a material consisting essentially of protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993. The term food includes a beverage adapted for human or animal consumption. As used herein a "food additive" is as defined by the FDA in 21 C.F.R. 170.3(e)(1) and includes direct and indirect additives. As used herein, a "pharmaceutical" is a medicinal drug. See Merriam-Webster's Collegiate Dictionary, 10th Edition, 1993. A pharmaceutical may also be referred to as a medicament. As used herein, a "dietary supplement" is a product (other than tobacco) that is intended to supplement the diet that bears or contains the one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients.

Any conventional food including any beverage which has been improved by the presence of a cocoa polyphenol or a derivative thereof, e.g. methylated compounds or metabolic breakdown products, and optionally in combination with a cholesterol lowering agent, L-arginine, calcium, potassium, magnesium, an oxidant such as vitamin E and vitamin C, any of the vitamins of the B complex, a carotenoid, guar gum, and/or a mono or polyunsaturated fatty acid (e.g. omega-3), is within the scope of the invention.

The improvement is achieved either (i) by adding cocoa polyphenol or a derivative thereof to a food that does not contain cocoa polyphenol or (ii) when the food traditionally may contain cocoa polyphenols, such as for example chocolate, by enhancing the polyphenol level over the one found in the traditionally prepared food. The enhancement may be achieved by adding additional cocoa polyphenols, for example, in a form of an extract, fraction or isolated and purified compound there from; by adding cocoa polyphenol in combination with another polyphenol containing ingredient (e.g. nut skins); by manipulating the cocoa ingredients processing and cocoa bean selection, as described above, to preserve cocoa polyphenol in the cocoa ingredient used for the manufacture of the food product; or by manipulating the chocolate manufacturing process as described above. Thus, these foods (including beverages) contain an "elevated level of polyphenols" (including cocoa procyanidins) in comparison to comparative conventional foods (including beverages). An example of a chocolate having an elevated level of polyphenol occurs when a chocolate manufacturer adds a cocoa extract containing cocoa polyphenols to its previously commercially available product. The foods may also be referred to as "high cocoa polyphenol foods," i.e., they contain higher levels of polyphenol than their traditional counterparts.

The foods comprising cocoa polyphenols and optionally at least one cholesterol lowering agent (e.g. a sterol and/or stanol based cholesterol lowering agent), L-arginine, calcium, potassium, magnesium, an antioxidant such as vitamin E and vitamin C, any of the vitamins of the B complex, a carotenoid, guar gum, or a mono or polyunsaturated fatty acid (e.g. omega-3) may be adapted for human or veterinary use, and include pet foods. The food may be other than a confectionery, however, the preferred cholesterol lowering food is a confectionery such as a standard of identity (SOI) and non-SOI chocolate, such as milk, sweet and semi-sweet chocolate including dark chocolate, low fat chocolate and a candy which may be a chocolate covered candy. Other examples include a baked product (e.g. brownie, baked snack, cookie, biscuit) a condiment, a granola bar, a toffee chew, a meal replacement bar, a spread, a syrup, a powder beverage mix, a cocoa or a chocolate flavored beverage, a pudding, a rice cake, a rice mix, a savory sauce and the like. If desired, the foods may be chocolate or cocoa flavored. Food products that contain L-arginine, in addition to the cocoa polyphenol and the cholesterol lowering agent, are preferably chocolates and candy bars, such as granola bars, containing nuts, for example, peanuts, walnuts, almonds, and hazelnuts. It should be noted that the addition of nuts with skins to the food described herein may also increase the total polyphenol content since, for example, peanut skins contain about 17% flavanols and procyanidins and almond skins contain about 30% flavanols and procyanidins. In one embodiment, the nut skins are added to the nougat of a chocolate candy containing a cholesterol lowering agent.

In certain embodiments, the non-chocolate food product contains from about at least 5 micrograms/g to about 10 mg/g, and, for example, at least 5 micrograms/g food product, preferably at least 10 microgram/g, more preferably at least 100 micrograms/g of cocoa flavanols and/or procyanidin oligomers. If desired, the non-chocolate food products can contain much higher levels of cocoa procyanidins than those found in the chocolate food products described below.

In one embodiment, a chocolate confectionery contains an effective amount of cocoa flavanol and/or procyanidin to treat, prevent, reduce the risk of, or reduce the occurrences of heart arrhythmia, or generally any condition associated with abnormalities in gap junctional communication, such as for example, a neuro-degenerative disease. The chocolate confectionery may be milk or dark chocolate. In certain embodiments, the chocolate comprises at least 3,600 micrograms, preferably at least 4,000 micrograms, preferably at least 4,500 micrograms, more preferably at least 5,000 micrograms, and most preferably at least 5,500 micrograms cocoa flavanols and/or procyanidins each per gram of chocolate, based on the total amount of nonfat cocoa solids in the product. In other embodiments, the chocolate contains at least 6,000 micrograms, preferably at least 6,500 micrograms, more preferably at least 7,000 micrograms, and most preferably at least 8,000 micrograms of cocoa procyanidins per gram, and even more preferably 10,000 micrograms/g based on the nonfat cocoa solids in the product.

A milk chocolate confectionery may have at least 1,000 micrograms, preferably at least 1,250 micrograms, more preferably at least 1,500 micrograms, and most preferably at least 2,000 micrograms cocoa flavanols and/or procyanidins each per gram of milk chocolate, based on the total amount of nonfat cocoa solids in the milk chocolate product. In the preferred embodiment, the milk chocolate contains at least 2,500 micrograms, preferably at least 3,000 micrograms, more preferably at least 4,000 micrograms, and most preferably at least 5,000 micrograms cocoa flavanols and/or procyanidins each per gram of milk chocolate, based on the total amount of nonfat cocoa solids in the milk chocolate product.

The amount of L-arginine in the food products can vary. Typically, cocoa contains between 1 to 1.1 grams of L-arginine per 100 grams of partially defatted cocoa solids. It can range from 0.8 to 1.5 per 100 grams of cocoa. The chocolate food products of this invention contain L-arginine in an amount greater than that which naturally occurs in the cocoa ingredients. Knowing the amount of cocoa ingredients and L-arginine used in the food product, one of ordinary skill in the art can readily determine the total amount of L-arginine in the final product. The food product will generally contain at least 5 micrograms/g, preferably at least 30 micrograms/g, or at least 60 micrograms/g, even more preferably at least 200 micrograms/g food product.

When the cholesterol lowering agent is used in the food, its amount will depend on the type of the agent used and can be determined by a person of skill in the art based on the guidance in the specification, particularly daily dosages provided below, and the knowledge in the art. A food composition, for example, may contain from about 0.5 to about 10 g per 45 g serving size, preferably about 1.5 to about 5 g per 45 g serving size, most preferably about 2 to about 4.5 g per 45 g serving size of sterols/stanols. With respect to soy protein and soluble fiber from oats, FDA has provided minimum amounts per food serving to be able to make a health claim. According to the FDA, a food serving containing beta-glucan must contain at least 0.75 g, and the food serving containing soy protein must contain at least 6.25 g soy protein. These values may also be used as a guide for determining the amount of these cholesterol lowering agents in the food.

A daily effective amount of cocoa flavanols and/or procyanidins may be provided in a single serving. Thus, a confectionery (e.g. chocolate) may contain at least about 100 mg/serving (e.g. 150-200, 200-400 mg/serving) cocoa procyanidins. When the cholesterol lowering agent is included in the composition, at least 1.5 (e.g. 1.5-4.5 g) per serving sterol/stanol may be added.

Pharmaceuticals containing cocoa flavanols and/or procyanidins, optionally in combination with a cholesterol lowering agent and/or L-arginine, may be administered in a variety of ways such as orally, sublingually, bucally, nasally, rectally, intravenously, parenterally and topically. A person of skill in the art will be able to determine a suitable cholesterol lowering agent depending on the mode of administration. Thus, dosage forms adapted for each type of administration are within the scope of the invention and include solid, liquid and semi-solid dosage forms, such as tablets, capsules, gelatin capsules (gelcaps), bulk or unit dose powders or granules, emulsions, suspensions, pastes, creams, gels, foams or jellies. Sustained-release dosage forms are also within the scope of the invention and may be prepared as described in U.S. Pat. Nos. 5,024,843; 5,091,190; 5,082,668; 4,612,008 and 4,327,725, relevant portions of which are hereby incorporated herein by reference. Suitable pharmaceutically acceptable carriers, diluents, or excipients are generally known in the art and can be determined readily by a person skilled in the art. The tablet, for example, may comprise an effective amount of the cocoa polyphenol-containing composition and optionally a carrier, such as sorbitol, lactose, cellulose, or dicalcium phosphate.

The dietary supplement containing cocoa flavanol and/or procyanidin, and optionally at least one cholesterol lowering agent and/or L-arginine, may be prepared using methods known in the art and may comprise, for example, nutrient such as dicalcium phosphate, magnesium stearate, calcium nitrate, vitamins, and minerals.

Further within the scope of the invention is a package comprising the composition of the invention (e.g. a food, a dietary supplement, a pharmaceutical) and a label indicating the presence of, or an enhanced content of cocoa flavanol and/or procyanidin and/or a derivative thereof, or directing use of the composition to treat, prevent, reduce the occurrences of, or reduce the risk of heart arrhythmia or any condition associated with the abnormality in the cellular gap junction communication, such as a neuro-degenerative disease. Optionally, the label may indicate the cholesterol lowering agent and/or L-arginine content, the beneficial properties of the combined polyphenol(s), cholesterol lowering agent(s) and optionally L-arginine. The package may contain the composition and the instructions for use to treat, prevent, reduce the risk of, slow progression or reduce the occurrences of heart arrhythmia or any condition associated with the abnormality/defect in the cellular gap junction communication, such as a neuro-degenerative disease or cancer.

As used herein, "treatment" means improving an existing medical condition, for example, heart arrhythmia, or the symptoms associated therewith. The term "preventing" means reducing the risks associated with developing a disease, including reducing the onset of the disease. The prevention or prophylaxis may be used in an individual known to be at high risk of developing a disease or in a population at large for maintaining good health, for example, reducing the risk of arrhythmia. The methods may be used in a human or a veterinary animal, such as a dog, a cat, and a horse.

The methods comprise administering to a mammal, preferably a human or a veterinary animal, for an effective period of time (for example, to induce de novo connexin synthesis), an amount of the composition comprising a flavanol and/or its related oligomer, such as a cocoa flavanol and/or its related oligomer, optionally in combination with a cholesterol lowering agent, L-arginine, an antioxidant (e.g. vitamin E, vitamin C), the flavanol and/or its related oligomer being in the amount effective to treat, prevent or reduce the occurrences of heart arrhythmia or any condition associated with the gap junctional abnormalities/defects, e.g. neuro-degenerative diseases (such as Parkinson's and Alzheimer's). Moreover, treatment of cognitive dysfunctions which are connexin, for example, connexin 40 and/or 43, related is also within the scope of the invention. Thus, connexin related functions may be treated or improved. Examples of cognitive dysfunctions that may be treated according to the invention are short term memory and depression. Other polyphenols such as those isolated from peanut skins may also be used.

Thus, the following use is within the scope of the invention. Use of a cocoa flavanol and/or its oligomer in the manufacture of a medicament, food, nutraceutical or dietary supplement for use in treating, preventing, reducing the risk of, or reducing the progression of a disease involving defective gap junctional communication in a human or a veterinary animal.

The following uses are representative of some embodiments. Use of a cocoa flavanol and/or its oligomer in the manufacture of a medicament, food, nutraceutical or dietary supplement for use in treating, preventing, reducing the risk of, or reducing the occurrence of heart arrhythmias in a human or a veterinary animal. Use of a cocoa flavanol and/or its oligomer in the manufacture of a medicament, food, nutraceutical or dietary supplement for use in treating, preventing, reducing the risk of, or reducing the progression of a cognitive dysfunction in a human or a veterinary animal.

A polymeric compound of the formula $A_n$, or a pharmaceutically acceptable salt thereof, may be used in the compositions and uses of the present invention:

wherein n is an integer from 2 to 18, such that there is at least one terminal monomeric unit A, and one or a plurality of additional monomeric units;

R is 3-(α)-OH, 3-(β)-OH;

bonding between adjacent monomers takes place at positions selected from the group consisting of 4, 6 and 8;

a bond of an additional monomeric unit in position 4 has alpha or beta stereochemistry;

X, Y and Z are selected from the group consisting of monomeric unit A or hydrogen, with the provisos that as to the at least one terminal monomeric unit, bonding of the additional monomeric unit thereto is at position 4 and optionally Y=Z=hydrogen.

The effective amount may be determined by a person of skill in the art using the guidance provided herein. For example, the effective amount may be such as to achieve a physiologically relevant concentration in the body of a mammal. Such a physiologically relevant concentration may be at least 20 nanomolar (nM), preferably at least about 100 nM, and more preferably at least about 500 nM. In one embodiment, at least about one micromole in the blood of the mammal is achieved.

The methods may further comprise determining the effectiveness of the treatment by, for example, determining the heart beat, such as using electrocardiogram (ECG), ambulatory monitors, holter monitors, transtelephonic monitors (optionally with memory loop), stress test, echocardiogram, cardiac catheterization, electophysiology study and head upright tilt test.

The composition may be administered to a healthy mammal for prophylactic purposes or to a mammal in need of a treatment or having at least one of the risk factors associated with heart arrhythmia. Any individual having at least one of the risk factors associated with heart arrhythmia is a subject for administration of the compositions described herein. The individuals with a familial history of heart arrhythmia, hypertension, coronary artery disease, heart attack, abnormal thyroid function as well as those smoking, and having alcohol, caffeine, or illegal substance intake (e.g. cocaine), or those recovering from heart surgery, are susceptible individuals in need of the treatment described herein. Other populations of mammals that are susceptible to developing vascular health problems will be apparent to a person of skill in the art.

Veterinary animal, for example dogs, cats and horses, may be administered the above described compositions to treat, prevent or reduce the occurrences of heart arrhythmia.

The effective amount to treat, prevent, reduce the risk of and/or reduce the occurrences of heart arrhythmia may be determined by a person skilled in the art using the guidance provided herein and the general knowledge in the art. Cocoa flavanols and/or related oligomers may be administered at from about 50 mg/day to about 1000 mg/day, preferably from about 100-150 mg/day to about 900 mg/day, and most preferably from about 300 mg/day to about 500 mg/day. However, given that cocoa polyphenols are non-toxic, amounts higher than stated above may be used.

To additionally obtain a cholesterol lowering effect, using sterols/stanols, more than what is normally found in the average diet of a non-vegetarian should be administered. A person on a typical North American diet consumes about 200-400 mg/day. Thus, when phytosterol, such as sitosterol, is used to reduce cholesterol levels, about at least 1 g/day, preferably at least about 3 g/day should be administered. Preferably, from at least about 1 g/day, preferably at least about 4.5 g/d, to about 20 g/day is used. However, the amount will vary depending on the cholesterol lowering potency of the phytosterol so that, for example, if a more potent sitostanol is used, the effective amount may be as low as about one to about three g/day. The amounts may be determined using the analytical procedure described in Roger et al., J. Amer. Oil Chem. Soc. 70(30) 1993 and Carpenter, et al., J. Amer. Oil Chem. Soc. 71 (8) 1994. Soy protein may be administered, for example, at least about 25 g/day. Further guidance can be found in Recommended Daily Allowances, $9^{th}$ ed., National Res. Council/National Acad. Sci., Washington, D.C. Soluble fiber may be administered, for example, in the amount of at least 3 g/day.

L-arginine, when used in the compositions and the treatment, may be administered from about 2 g/day to about 50 g/day, preferably from about 3 g/day to about 10 g/day, and most preferably from about 6 g/day to about 8 g/day. Here as well, given that L-arginine naturally occurs in foods, amounts higher than stated above may be used. Polyphenols generally may be administered in the amounts known in the art. The enhanced absorption in the presence of sterols/stanols may also be taken into consideration when determining the effective amount.

The treatments/preventive administration may be continued as a regimen, i.e., for an effective period of time, e.g., daily, monthly, bimonthly, biannually, annually, or in some other regimen, as determined by the skilled medical practitioner for such time as is necessary. The administration may be continued for at least a period of time required to induce connexin synthesis. Preferably, the composition is administered daily, most preferably two or three times a day, for example, morning and evening to maintain the levels of the effective compounds in the body of the mammal. To obtain the most beneficial results, the composition may be administered for at least about 30 to about 60 days. These regiments may be repeated periodically.

The invention is further described in the following non-limiting examples.

EXAMPLES

Example 1

The Effects of Cocoa Flavanol/Procyanidin on Gap Junctional Communication of Cells Cell Culture.

WB-F344 rat liver epithelial cells (kindly provided by Dr. Trosko, East Lansing, Mich.) were grown in Dulbecco's modification of Eagle's Medium (DMEM) supplemented with 10% fetal calf serum (FCS), 2 mM L-glutamine and penicillin/streptomycin in 35 mm plastic dishes. Cells were incubated at 37° C. in a humidified atmosphere containing 5% $CO_2$. The confluent cells were incubated with DMEM (without FCS) for 24 h to decrease the basal level of cell-cell communication. (−)-Epicatechin, genistein (Sigma) or TPA were dissolved in DMSO and added to the medium; controls received DMSO only. The final concentration of DMSO in the medium was 0.2%. The epicatechin dimer was prepared as described in Adamson et al. ("HPLC Method for the Quantification of Procyanidins in Cocoa and Chocolate Samples and Correlation to Total Antioxidant Capacity" J. Ag. Food Chem., Vol. 7:10, 4184-4188), the relevant portion of which is hereby incorporated herein by reference.

Gap Junctional Communication Assay.

Cells were treated with (−)-epicatechin (4 to 40 µM) and genistein (40 µM) for 24 and 72 h and GJIC was determined. For the experiments with TPA, incubation was for 90 min with TPA (1, 5, 10 nM), TPA (1, 5, 10 nM) plus epicatechin (40 µM), and TPA (1, 5, 10 nM) plus genistein (40 µM); DMSO (0.2%) was used as a control. GJIC was measured by microinjection of the fluorescent dye Lucifer Yellow CH (10% in 0.33 M LiCl) into selected cells by means of a micromanipulator and a microinjector system (Eppendorf). One min after injection, the number of fluorescent cells around a single cell which was loaded with the dye were counted. Ten individual cells were injected per dish and means of the number of fluorescent neighboring cells were calculated. Images were taken with a Zeiss axiovert fluorescent microscope coupled to a CCD camera (ORCA II, Hamamatsu).

Western Blot Analysis.

To obtain cell lysate, WB-F344 rat liver epithelial cells were washed with PBS (2.7 mM KCl, 1.5 mM $KH_2PO_4$, 137 mM NaCl, 10 mM $Na_2HPO_4$; pH 7.4) and treated two times with SDS-PAGE lysis buffer (125 mM Tris, 4% SDS, 20% glycerol, 100 mM dithiothreitol, 0.2% bromophenol blue; pH 6.8). After sonication the lysates were heated for 5 min at 95° C. and applied to SDS-polyacrylamide gel electrophoresis (10% (w/v) acrylamide). The gels were blotted onto polyvinylidene difluoride (PVDF) membranes. Immunodetection was performed with a polyclonal rabbit anti-Cx43 antibody (Zymed) as primary antibody and goat anti-rabbit IgG (Dianova) as secondary antibody.

Immunohistochemistry.

For immunohistochemistry, WB-F344 cells were grown in complete medium with FCS on coverslips in 35 mm plastic dishes until they reached 90% confluence. The cells were incubated for 90 min with 1, 5, or 10 nM TPA, 40 µM (−)-epicatechin or 40 µM genistein or a combination of 40 µM (−)-epicatechin and (1, 5, 10 nM) TPA or 40 µM genistein and (1, 5, 10 nM) TPA; DMSO (0.2%) was used as a control. After treatment, cells were washed with PBS and fixed with methanol for 10 min at −20° C. After further washing with PBS, non-specific binding sites were blocked with 3% normal goat serum (NGS) in PBS containing 0.3% (v/v) Triton-X-100 for 45 min at room temperature. Cells were incubated with a polyclonal anti-Cx 43 antibody (Zymed); diluted 1:1500 in PBS with 1% (v/v) NGS overnight at 4° C. Cells were washed with PBS, and incubated with an Alexa 546-coupled goat anti-rabbit Ig G (H+L) secondary antibody (Molecular Probes; diluted to 1:800 in PBS) for 45 min at 37° C. After washing and embedding, images were taken with a Zeiss axiovert fluorescent microscope coupled to a CCD camera (ORCA II, Hamamatsu).

Results

Genistein affects GJIC in cell culture at levels above 10 µM [Zhang Y W, Morita I, Nishida M, Murota S I. Involvement of tyrosine kinase in the hypoxia/reoxygenation-induced gap junctional intercellular communication abnormality in cultured human umbilical vein endothelial cells. J Cell Physiol 1999; 180:305-13.].

Figure 1:
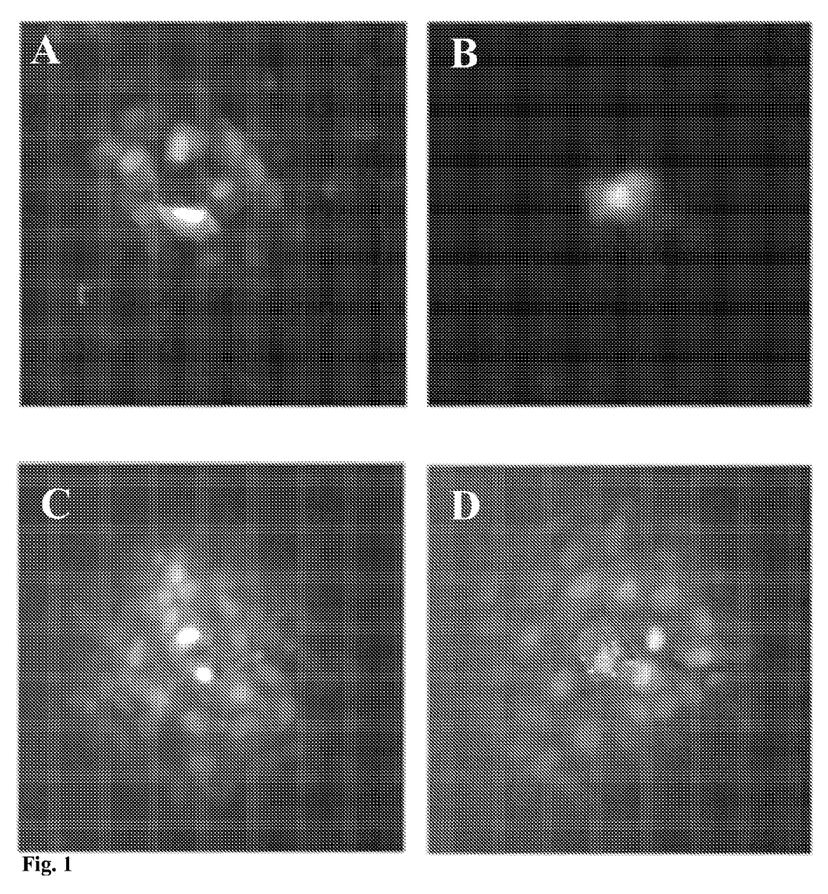
FIG. 1A-D represents the gap junctional intercellular communication in WB-F344 cells measured by the Lucifer Yellow dye transfer assay. A: control (0.2% DMSO); B: TPA 10 nM (90 min); C: genistein 40 µM (72 h); D: (−)-epicatechin 40 µM (72 h).

In the present study, the exposure of WB-F344 rat liver epithelial cells to genistein or epicatechin (40 µM) led to a stimulation of GJIC which was dependent on the time of incubation. After 24 h of exposure the stimulation of GJIC with genistein and (−)-epicatechin was 2.1-fold and 1.5-fold of control, respectively. Upon incubation for 72 h the increase was 2.9-fold above controls for genistein and 2.1-fold for (−)-epicatechin. The controls were treated with DMSO (0.2%) only; baseline communication was 13.4±1.0 cells at 24 h and 12.1±1.3 cells at 72 h. FIG. 1 shows typical examples of communication measurements with the dye transfer assay; control (FIG. 1A), inhibition with TPA (10 nM) after 90 min (FIG. 1B), stimulation with genistein (FIG. 1C) or (−)-epicatechin (FIG. 1D) at 40 µM after 72 h of treatment.

Both flavonoids showed no significant effect on GJIC after 90 min incubation. With increasing levels of (−)-epicatechin in cell culture (4 to 40 µM), the number of communicating cells was increased (Table 1). In cells treated with the lowest concentration (4 µM) the communication was still 1.6-fold above solvent control. The dimeric form of the epicatechin tested at the 20 µM level stimulated GJIC to about the same level as 40 µM of the monomer.

TABLE 1

Effects of (−)-epicatechin and genistein on GJIC in WB-F344 rat liver.

| Compound | | Number of communicating cells | % of Control |
|---|---|---|---|
| Control | (0.2% DMSO) | 12.1 ± 1.3 | 100 ± 11 |
| (−)-Epicatechin | 4 µM | 18.1 ± 2.2* | 156 ± 18* |
| | 10 µM | 20.1 ± 6.8* | 173 ± 56* |
| | 40 µM | 24.2 ± 3.1* | 209 ± 26* |
| Epicatechin dimer | 20 µM | 23.4 ± 3.1* | 202 ± 26* |
| Genistein | 40 µM | 35.4 ± 2.4* | 293 ± 20* |

*significantly different from control (p < 0.001)
Cells were exposed to different concentration of (−)-epicatechin (4-40 µM). Genistein was measured at 40 µM. Communication was determined after 72 h of incubation. GJIC is given as numbers of communicating cells measured by the dye transfer assay and as % of control. Controls were treated with DMSO (0.2%); basal communication was 12.1 ± 1.3 cells which was set to 100%. The data represent means ± SD of 3 independent experiments.

TPA affects GJIC by modification of the Cx43 protein. Since Cx43 is a major gap junction protein in WB344 cells, we investigated the effects of TPA on GJIC in the presence of (−)-epicatechin and genistein (Table 2). When the cells were exposed for 90 min to TPA alone, intercellular communication was completely disrupted at levels of 5 and 10 nM (FIG. 1B); GJIC was diminished by about 40% when 1 nM TPA was used. No effect was found with 0.1 nM TPA. In all experiments cell viability was not affected. The incubation of cells with TPA for 72 h had no effect on GJIC; the number of communicating cells was comparable to the control, i.e., there was a complete recovery from the loss observed at 90 min.

TABLE 2

Inhibitory effects of TPA on GJIC; counteraction by (−)-epicatechin and genistein.

| TPA (nM) | TPA (% control) | TPA plus (−)-epicatechin 40 μM (% control) | TPA plus genistein 40 μM (% control) |
|---|---|---|---|
| 0.1 | 94 ± 14 | 95 ± 14 | n.m. |
| 1 | 55 ± 19 | 95 ± 19* | 90 ± 23* |
| 5 | 0 | 61 ± 15* | 83 ± 18* |
| 10 | 0 | 50 ± 16* | 72 ± 17* |

*significantly different from treatment with TPA ($p < 0.001$) means ± SD (n = 3)
n.m.: not measured
Cells were exposed to different levels of TPA and combinations of different amounts of TPA with either 40 μM (−)-epicatechin or 40 μM genistein. GJIC is presented as % of control. Controls were treated with DMSO (0.2%); basal communication was 18.6 +/− 2.9 cells which was set to 100%. Communication was measured after 90 min of incubation. The data represent means +/− SD of 3 independent experiments.

The complete loss of GJIC by TPA after 90 min (5 and 10 nM) was partially counteracted when TPA was coincubated with 40 μM of (−)-epicatechin or genistein. Genistein was slightly more effective than (−)-epicatechin. Both compounds restored GJIC to basal levels when applied together with 1 nM of TPA.

Figure 2:
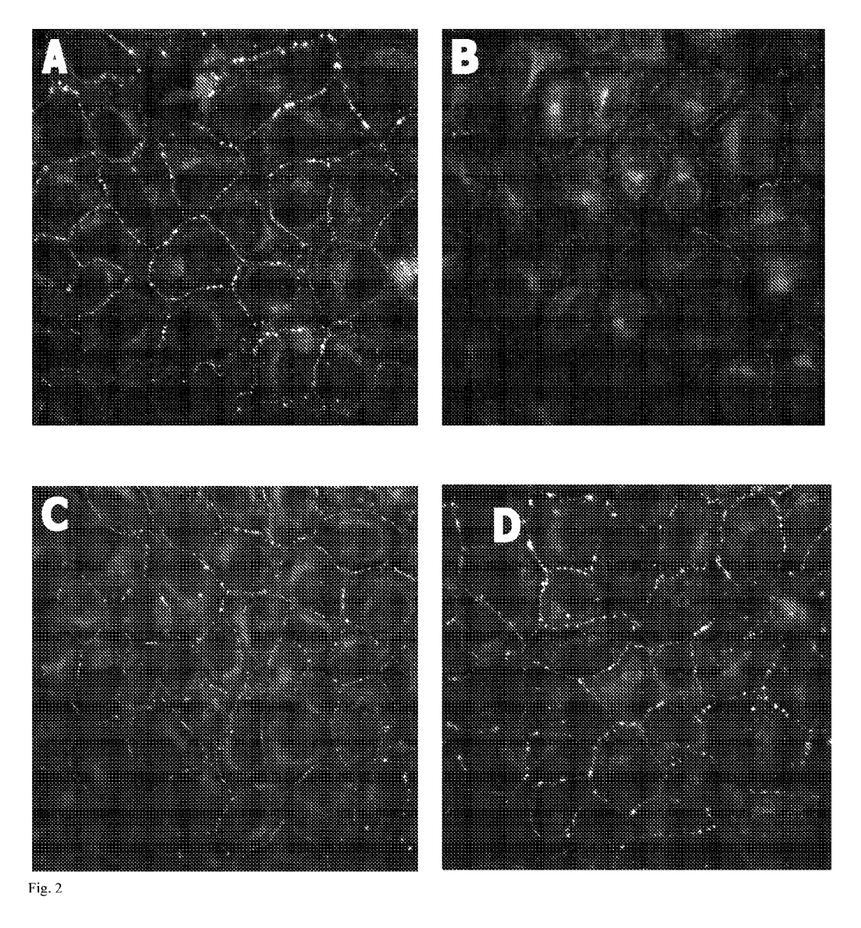
FIG. 2A-D represents the immunofluorescence analysis of the subcellular distribution of connexin43. A: control (0.2% DMSO); B: TPA 10 nM; C: TPA 10 nM plus (−)-epicatechin 40 µM; D: TPA 10 nM plus genistein 40 µM. Incubation time for all treatments was 90 min.

In parallel, the distribution of Cx43 protein within the cells was investigated by immunostaining (FIG. 2). A typical control is shown in FIG. 2A. The cells are confluent, and connexin proteins are localized at the plasma membrane. Some protein signal is also detectable within the cytoplasm. Upon treatment with TPA for 90 min (10 nM), the signal of membrane-associated Cx43 decreased dramatically (FIG. 2B), no more areas of accumulated Cx43 protein being detectable. When (−)-epicatechin (FIG. 2C) or genistein (FIG. 2D) was present in cell culture, the TPA effect was attenuated. Cx43 protein was detectable in the membrane organized in clustered structures comparable to the control (FIG. 2A). Similar counteracting effects of (−)-epicatechin and genistein were found when TPA was used at 1 and 5 nM.

Example 2

Determination of Flavanols/Procyanidins

Procyanidins were quantified as follows: a composite standard was made using commercially available (−)-epicatechin, and dimers through decamers obtained in a purified state by the methods described in Hammerstone, J. F. et al., *J. Ag. Food Chem.*; 1999; 47 (10) 490-496; Lazarus, S. A. et al., *J. Ag. Food Chem.*; 1999; 47 (9); 3693-3701; and Adamson, G. E. et al., *J. Ag. Food Chem.*; 1999; 47 (10) 4184-4188. Standard Stock solutions using these compounds were analyzed using the normal-phase HPLC method described in the previously cited Adamson reference, with fluorescence detection at excitation and emission wavelengths of 276 nm and 316 nm, respectively. Peaks were grouped and their areas summed to include contributions from all isomers within any one class of oligomers and calibration curves were generated using a quadratic fit. Monomers and smaller oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was defatted using three hexane extractions (45 mL each). Next, one gram of defatted material was extracted with 5 mL of the acetone/water/acetic acid mixture (70:29.5:0.5 v/v). The quantity of procyanidins in the defatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

Example 3

The Effect of Oral Consumption of Cocoa Procyanidins, Phytosterols and the Combination Thereof The results of this experiment show the effects of feeding a combination of non-esterified phytosterols and phytostanols available from tall oil ("phytosterol") and cocoa powder (CPd), containing about 70 mg/g of total cocoa procyanidins, on (1) indices of oxidative stress and damage, and (2) on cholesterol levels, as well as the synergistic effect of the combined administration of phytosterols and cocoa procyanidins.

A purified egg shell diet was supplemented with phytosterols (2 wt %) and/or CPd (0, 0.5, 1, 2 wt %) and used to feed male rats for a period of 2 weeks. The rats were divided in eight groups (three rats per group) and fed 20-25 g/day of the control and test diets according to the following:

| Diet + 2% phytosterol (440 mg/d) | | Diet-phytosterol | |
|---|---|---|---|
| Group 1 | 0% CPd(0.0 mg/d) | Group 5 | 0% CPd(0.0 mg/d) |
| Group 2 | .5% CPd(110 mg/d) | Group 6 | .5% CPd(110 mg/d) |
| Group 3 | 1% CPd(220 mg/d) | Group 7 | 1% CPd(220 mg/d) |
| Group 4 | 2% CPd(440 mg/d) | Group 8 | 2% CPd(440 mg/d) |

Water was fed ad lib and consumption was determined by weighing leftover/spilled food collected underneath the food cups. The food intake was measured daily and the rat weight every other day.

The oxidative damage/stress parameters, cholesterol levels and the epicatechin absorption into the blood plasma were measured.

Plasma TBARS were measured using a modification of the method described by Yagi (Biochem Med 15:212-6. 1976). One hundred μL of whole blood was added to one ml of physiological saline and centrifuged at 1700 g for 15 minutes. The supernatant was collected and frozen at −70° C. until analyzed. Lipids were isolated by precipitating them with a phosphotungstic acid/sulfuric acid system. The lipid fraction was then reacted with thiobarbituric acid, and the resulting adducts measured fluorimetrically, using 1,1',3,3'-tetraethoxypropane as the standard. Results were expressed as nanomoles of MDA per milliliter plasma and as a function of the concentration of plasma polyunsaturated fatty acids.

The 8-Hydroxy-2'-deoxyguanosine (8OH2'dG) was measured as follows. Nuclear DNA was isolated using the Wako DNA Extractor WB kit (Wako Chemical USA, Inc., Richmond, Va.). Tissue (100-250 mg) or cells ($10^6$ cells) were homogenized in the kit lysis buffer and centrifuged at 10,000 g for 20 seconds at 4° C. The pellet was treated with the lysis buffer and the resulting pellet dissolved in the kit enzyme reaction solution. RNase was added to a final concentration of 20 μg/ml and the sample was incubated at 50° C. for 10 minutes. The kit proteinase solution was added and the 50° C. incubation was continued for an additional hour. The sample was centrifuged at 10,000 g for five minutes at room temperature and the supernatant was treated with the kit NaI solution and isopropanol to purify the DNA. The precipitate was collected at 10,000 g for 10 minutes at room temperature and washed with the kit solutions A and B. The final pellet was briefly air-dried and resuspended in 200 μl of 0.1 mM desferyl/20 mM Na acetate, pH 4.8. The DNA digestion and analysis was carried out according to the method of Shigenaga et al. (Methods Enzymol 234:16-33, 1994) with some modification. Briefly, DNA was digested to nucleotide 5'-monophosphates by incubation with Nuclease P1 at a final concentration of 0.1 mg/ml for 15 minutes at 65° C. The pH was adjusted with 1 M Tris-HCl, pH 8.5, and calf intestine alkaline phosphatase was used to further digest the sample to nucleotides (one hour, 37° C.). The pH of the sample was adjusted with 3 M sodium acetate buffer, pH 5.1, and 0.1 mM EDTA/0.1 mM desferyl was added to prevent metal-mediated oxidation. The sample was put through a 30,000 MW cutoff spin filter and placed in an HPLC injection vial. Samples were analyzed within 48 hours of preparation to prevent artifact formation. For analysis, samples were injected onto a Hewlett Packard 1100 HPLC equipped with an electrochemical detector (ESA, Coulochem II). Separation was achieved using a Supelcosil LC-18-DB column (150×4.6 mm, 3 micron particle size) and mobile phase of 100 mM Na acetate buffer, pH 5.2, with 5% methanol, isocratic, at a flow rate of 1.0 ml/min. $OH^8dG$ was detected at 450 mV using electrochemical detection and 2'-deoxyguanosine (dG) was detected at 248 nm using UV detection. Levels of $OH^8dG$ were expressed relative to the amount of dG in the samples.

Epicatechin absorption was measured as described in Rein et al., J. of Nutr., 2000, 130 (8S), 2109S-2114S.

Results

The results establish unexpected benefits of the combined administration of phytosterols and polyphenols.

Figure 3:
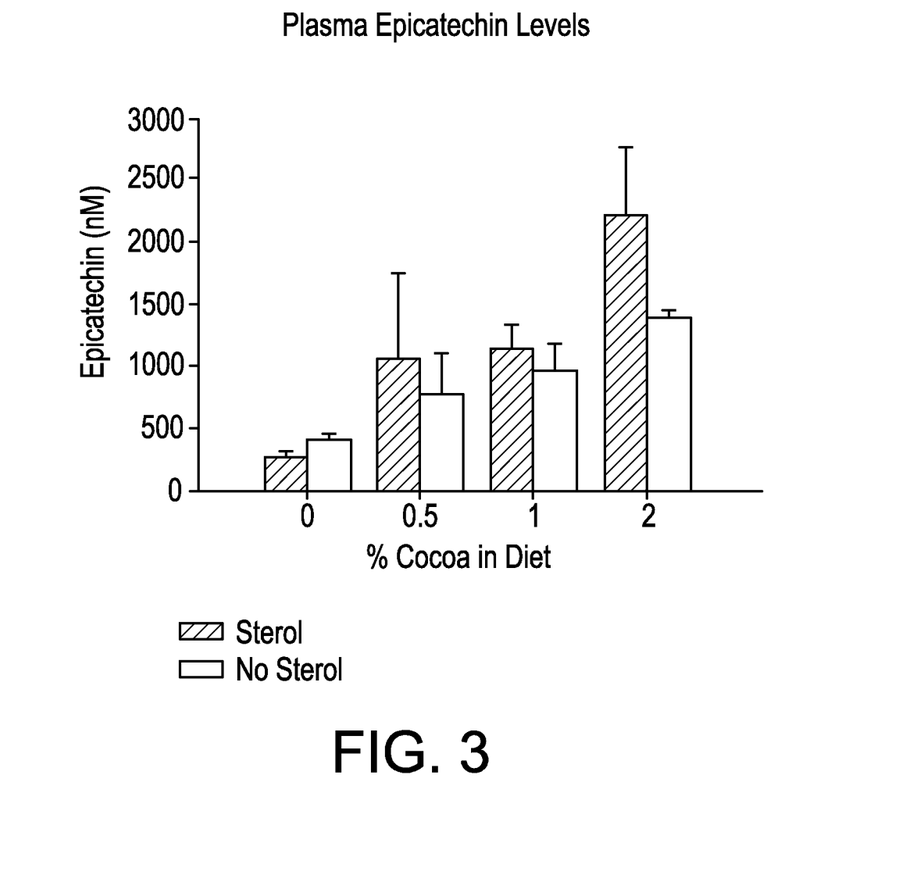
FIG. 3 shows the effects of the phytosterols, cocoa procyanidins and a combination thereof on the absorption of epicatechin into the blood plasma.

Referring to FIG. 3, the amount of the absorbed epicatechin increased in a dose dependent fashion. Surprisingly, the administration of phytosterols enhanced the absorption of epicatechin so that, for example, at 2 wt % CPd diet, the epicatechin plasma levels were enhanced by about 30% in comparison to the comparable diet without phytosterols. Hence, the phytosterol augmented the bioavailability of epicatechin.

Figure 4:
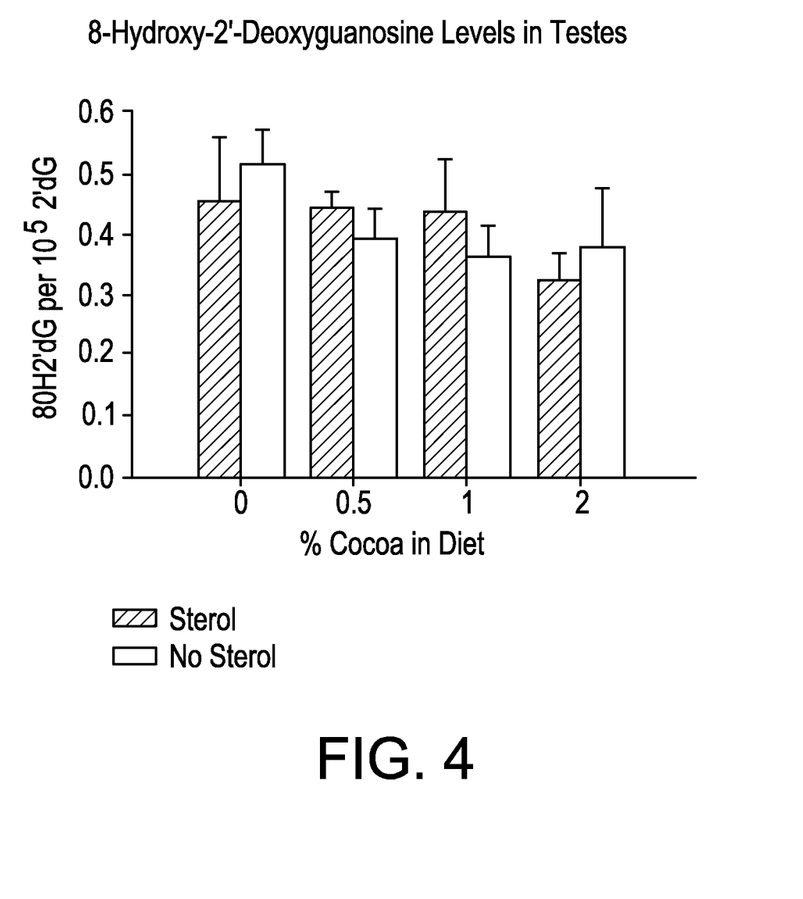
FIG. 4 shows the effects of the phytosterols, cocoa procyanidins and a combination thereof on the oxidative damage to DNA.

Referring to FIG. 4, CPd inhibited oxidative damage to DNA in a dose dependent manner. Surprisingly, at higher doses of CPd (2 wt %), an unexpected reduction in the oxidative damage to DNA was observed indicating a synergistic effect of phytosterols and CPd in preventing oxidative damage to DNA.

Figure 5:
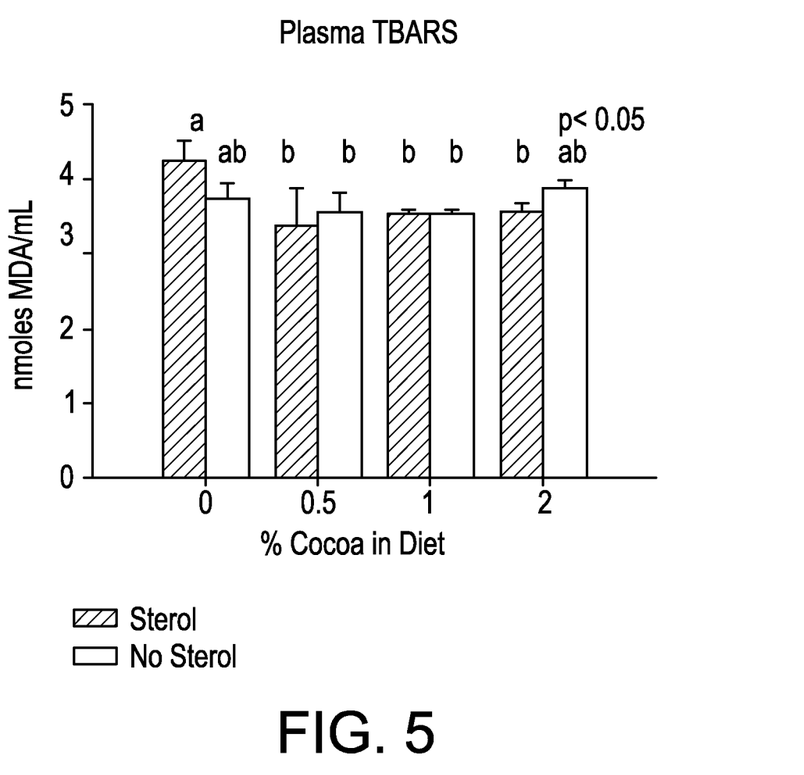
FIG. 5 shows the effects of the phytosterols, cocoa procyanidins and a combination thereof on the oxidative damage to lipids.

Referring to FIG. 5, feeding a diet containing phytosterols surprisingly caused a higher oxidative stress than the control diet, i.e., the intake of phytosterol together with food (without cocoa procyanidins), which was recommended in the art prior to the filing date of this application, exacerbated the oxidative stress. Feeding of cocoa procyanidins reversed or blunted this negative effect of phytosterols.

Total plasma cholesterol was also measured and the results are represented in Table 3.

TABLE 3

Total Plasma Cholesterol

|  | Count | Mean |
|---|---|---|
| 2% Sterol | 3 | 84,000 |
| 2% Sterol + 0.5% Coca | 2 | 84,500 |
| 2% Sterol + 1% Cocoa | 3 | 82,000 |
| 2% Sterol + 2% Cocoa | 3 | 80,000 |
| No Sterol + No Cocoa | 3 | 88,333 |
| 0.5% Cocoa | 3 | 82,667 |
| 1% Cocoa | 3 | 87,000 |
| 2% Cocoa | 3 | 81,667 |

Referring to Table 3, as expected, phytosterols reduced cholesterol levels. Surprisingly, however, when phytosterols were administered with CPd, the cholesterol levels decreased even more, in a dose dependent manner. For example, the mean total cholesterol level of the three rats fed a phytosterol-containing diet was 84 mg/dl. Supplementation of this diet with 2 wt % CPd resulted in an additional decrease of total cholesterol to 80 mg/dl, indicating a synergistic effect of the two compounds. The rats fed the control diet had a mean cholesterol level of 88.3 mg/dl.

Example 4

Food Compositions Containing Cholesterol Lowering Agents in Combination with Cocoa Procyanidin Containing Cocoa or Chocolate Dark chocolate, toffee chew and granola bars containing cholesterol lowering agents were prepared.

Toffee chew was prepared from the ingredients shown in Table 4 by pre-blending sugar and cocoa and mixing it with caramel. Free phytosterols (as is or pulverized) were added to the sugar and cocoa mix.

TABLE 4

Phytosterol-Containing Toffee Chews

|  | % Formula - range | % Formula | Phytosterols | Cocoa Procyanidins |
|---|---|---|---|---|
| Caramel | 55-65 | 63 |  |  |
| Cocoa | 20-30 | 22 |  |  |
| Sugar | 5-10 | 7.4 |  |  |
| Phytosterols | 5-12 | 7.5 |  |  |
| Total per 100 g |  |  | 7.5 | 550 |
| Total per 45 g serving |  |  | 3.375 | 248 |

Dark chocolate containing a free sterol was prepared using a commercially available dark chocolate (DOVE Dark available from Mars Inc.). To facilitate mixing with melted chocolate and to avoid any adverse effect on the chocolate texture, granulated forms of plant sterol/stanol were milled on Universal Muche M20, manufactured by IKA, for 30-60 seconds, mixed, and milled for another 30 seconds until the particle size became comparable to that of chocolate. Dark chocolate was melted and the sterol was added by slow mixing to ensure uniform distribution of sterol particles. The resulting composition is shown in Table 5.

TABLE 5

Phytosterol-Containing Dark Chocolate

|  | % Formula - range | % Formula | Phytosterols | Cocoa Procyanidins |
|---|---|---|---|---|
| Dark Chocolate | 88-95 | 92.5 |  |  |
| Phytosterols | 5-12 | 7.5 |  |  |
| Total per 100 g |  |  | 7.5 | 361 |
| Total per 45 g serving |  |  | 3.375 | 162 |

Granola bars containing cholesterol lowering oat fiber was prepared from the ingredients listed in Tables 6 and 7. The syrup binder was prepared by melting palm kernel oil to 45 C and was kept at that temperature until it was ready for use. Corn syrup, glycerin, cocoa powder, brown sugar, salt, lecithin, and propyl gallate were combined and the palm kernel oil added. The mixture was kept warm. To prepare granola, oats or soy puffs (available from Sovex Food, Collegedale, Tenn.) were blended with the chocolate pieces and the warm syrup binder prepared as described above was folded into the mixture. The granola mixture was then made into slabs, dusted with a mixture of 10× sugar (62%), cocoa powder (33%), and cinnamon (5%), and cut into pieces. The cocoa powder used in the mixture was prepared according to the method of U.S. Pat. No. 6,015,913 to Kealey et al.

TABLE 6

Granola Bar with Chocolate and Oats

|  | % Formula - range | % Formula | Oats | Cocoa Procyanidins |
|---|---|---|---|---|
| 63 DE Corn Syrup | 20-30 | 24.0 |  |  |
| Palm Kernel Oil | 0-4 | 3.2 |  |  |
| Glycerin | 2-3 | 2.4 |  |  |
| Cocoa Powder | 1-5 | 1.7 |  |  |
| Brown granulated Sugar | 1-2 | 1.3 |  |  |
| Salt | 0.2-0.5 | 0.3 |  |  |
| Lecithin | 0.1-0.5 | 0.1 |  |  |
| Propyl Gallate | 0.01-0.05 | 0.01 |  |  |
| Oats | 20-35 | 30 |  |  |
| Sugar | 0-20 | 11 |  |  |
| Vegetable Oil | 0-10 | 6 |  |  |
| Semi-sweet chocolate pieces | 10-30 | 20 |  |  |
| Total per 100 g |  |  | 30 | 150 |
| Total per 45 g serving |  |  | 13.5 | 68 |

TABLE 7

Granola Bar with Chocolate and Soy Protein

|  | % Formula - range | % Formula | Soy Protein | Cocoa Procyanidins |
|---|---|---|---|---|
| 63 DE Corn Syrup | 20-30 | 24.0 |  |  |
| Palm Kernel Oil | 0-4 | 3.2 |  |  |
| Glycerin | 2-3 | 2.4 |  |  |
| Cocoa Powder | 1-5 | 1.7 |  |  |
| Brownulated Sugar | 1-2 | 1.3 |  |  |
| Salt | 0.2-0.5 | 0.3 |  |  |
| Lecithin | 0.1-0.5 | 0.1 |  |  |
| Propyl Gallate | 0.01-0.05 | 0.01 |  |  |
| Soy Pieces | 50-60 | 52 |  |  |
| Semi-sweet chocolate pieces | 10-30 | 15 |  |  |

TABLE 7-continued

Granola Bar with Chocolate and Soy Protein

|  | % Formula - range | % Formula | Soy Protein | Cocoa Procyanidins |
|---|---|---|---|---|
| Total per 100 g |  |  | 20 | 125 |
| Total per 45 g serving |  |  | 9 | 56 |

What is claimed is:

1. A method of treating a subject suffering from cognitive dysfunction comprising administrating to the subject a composition in a unit dosage form comprising an effective amount of at least 50 mg of at least one compound having the formula $A_n$, a pharmaceutically acceptable salt thereof, and any mixture thereof:

wherein
A is epicatechin;
n is an integer from 2 to 18, such that there is at least one terminal monomeric unit A, and one or a plurality of additional monomeric units;
bonding between adjacent monomeric units takes place at positions selected from the group consisting of 4, 6 and 8;
a bond of an additional monomeric unit in position 4 has alpha or beta stereochemistry;
X, Y and Z are selected from the group consisting of monomeric unit A and hydrogen, with the proviso that as to the at least one terminal monomeric unit, bonding of the additional monomeric unit thereto is at position 4 and optionally Y=Z=hydrogen;
wherein the subject is a human or a veterinary animal, and wherein the composition comprises at least 50 mg of the at least one compound per unit dose.

2. The method of claim 1, wherein n is 2 to 12.
3. The method of claim 1, wherein n is 2 to 10.
4. The method of claim 3, wherein the composition is a pharmaceutical composition.
5. The method of claim 3, wherein the subject is a human.
6. The method of claim 5, wherein the human is in need of improving a short-term memory function.
7. The method of claim 5, wherein the effective amount is at least 100 mg/day.
8. The method of claim 5, wherein the effective amount is at least 150 mg/day.
9. The method of claim 5, wherein n is 2.
10. The method of claim 9, wherein the composition is a pharmaceutical composition.
11. The method of claim 9, wherein the composition is a food.
12. The method of claim 5, wherein the composition is a pharmaceutical composition.

13. The method of claim 5, wherein the food is a confectionery.

14. The method of claim 13, wherein the compound is provided within a cocoa extract.

15. The method of claim 13, wherein the compound is provided within a cocoa ingredient.

16. The method of claim 3, wherein the composition is a food.

17. The method of claim 16, wherein the compound is provided within a cocoa ingredient.

18. The method of claim 1, wherein the adjacent monomers bind at positions (4β→6) or (4β→8).

19. The method of claim 1, wherein n is 2.

20. The method of claim 1, wherein the compound is an epicatechin dimer.

21. The method of claim 1, wherein the composition is a pharmaceutical composition.

22. The method of claim 1, wherein the composition is a food.

23. The method of claim 1, wherein the composition is a pet food.

24. A method of treating a human subject suffering from cognitive dysfunction comprising administrating to the subject a composition in unit dosage form comprising an effective amount of a cocoa extract comprising at least 50 mg of at least one compound having the formula $A_n$ wherein A is epicatechin;

n is an integer from 2 to 10, such that there is at least one terminal monomeric unit A, and one or a plurality of additional monomeric units;

bonding between adjacent monomeric units takes place at positions selected from the group consisting of 4, 6 and 8;

a bond of an additional monomeric unit in position 4 has alpha or beta stereochemistry;

X, Y and Z are selected from the group consisting of monomeric unit A and hydrogen, with the proviso that as to the at least one terminal monomeric unit, bonding of the additional monomeric unit thereto is at position 4 and optionally Y=Z=hydrogen;

wherein the composition comprises at least 50 mg of the at least one compound per unit dose.

25. A method of improving cognitive function in a subject suffering from a neurodegenerative disease comprising administrating to the subject, as a regimen, a composition in unit dosage form comprising an effective amount of at least 50 mg of a of at least one compound having the formula $A_n$, a pharmaceutically acceptable salt thereof, and any mixture thereof:

wherein

A is epicatechin;

n is an integer from 2 to 18, such that there is at least one terminal monomeric unit A, and one or a plurality of additional monomeric units;

bonding between adjacent monomeric units takes place at positions selected from the group consisting of 4, 6 and 8;

a bond of an additional monomeric unit in position 4 has alpha or beta stereochemistry;

X, Y and Z are selected from the group consisting of monomeric unit A and hydrogen, with the proviso that as to the at least one terminal monomeric unit, bonding of the additional monomeric unit thereto is at position 4 and optionally Y=Z=hydrogen; and wherein the subject is a human or a veterinary animal, and wherein the composition comprises at least 50 mg of the at least one compound per unit dose.

26. The method of claim 25, wherein n is 2 to 12.

27. The method of claim 25, wherein n is 2 to 10.

28. The method of claim 27, wherein the composition is a pharmaceutical composition.

29. The method of claim 27, wherein the composition is a food.

30. The method of claim 29, wherein the compound is provided within a cocoa ingredient.

31. The method of claim 27, wherein the subject is a human.

32. The method of claim 31, where the neurodegenerative disease is Alzheimer's Disease.

33. The method of claim 32, wherein the composition is a pharmaceutical composition.

34. The method of claim 32, wherein n is 2.

35. The method of claim 31, where the neurodegenerative disease is Parkinson's Disease.

36. The method of claim 35, wherein n is 2.

37. The method of claim 31, wherein the effective amount is at least 100 mg/day.

38. The method of claim 31, wherein the effective amount is at least 150 mg/day.

39. The method of claim 31, wherein the composition is a pharmaceutical composition.

40. The method of claim 31, wherein n is 2.

41. The method of claim 40, wherein the composition is a pharmaceutical composition.

42. The method of claim 40, wherein the composition is a food.

43. The method of claim 31, wherein the composition is a confectionery.

44. The method of claim 43, wherein the compound is provided within a cocoa extract.

45. The method of claim 43, wherein the compound is provided within a cocoa ingredient.

46. The method of claim 25, wherein the adjacent monomers bind at positions (4β→6) or (4β→8).

47. The method of claim 25, wherein n is 2.

48. The method of claim 25, wherein the compound is an epicatechin dimer.

49. The method of claim 25, wherein the composition is a food.

50. The method of claim 25, wherein the composition is a pet food.

51. A method of improving cognitive function in a human subject suffering from a neurodegenerative disease comprising administrating to the subject, as a regimen, a composition in unit dosage form comprising an effective amount of a cocoa extract comprising at least 50 mg of at least one compound having the formula $A_n$:

wherein

A is epicatechin;

n is an integer from 2 to 10, such that there is at least one terminal monomeric unit A, and one or a plurality of additional monomeric units;

bonding between adjacent monomeric units takes place at positions selected from the group consisting of 4, 6 and 8;

a bond of an additional monomeric unit in position 4 has alpha or beta stereochemistry;

X, Y and Z are selected from the group consisting of monomeric unit A and hydrogen, with the proviso that as to the at least one terminal monomeric unit, bonding of the additional monomeric unit thereto is at position 4 and optionally Y=Z=hydrogen, wherein the composition comprises at least 50 mg of the at least one compound per unit dose.

* * * * *